United States Patent
Couse et al.

(10) Patent No.: US 11,937,579 B2
(45) Date of Patent: Mar. 26, 2024

(54) MONITORING AND IDENTIFYING LABORATORY ANIMALS THROUGH UWB AND OTHER DIGITAL SENSORY SIGNATURES

(71) Applicant: i4C Innovations Inc., Middleburg, VA (US)

(72) Inventors: John Michael Couse, Toronto (CA); Joe Paul Tupin, Jr., Round Hill, VA (US); Michael Stanfield, The Plains, VA (US); Albert Di Rienzo, Herndon, VA (US)

(73) Assignee: One Health Group, Inc., Cazenovia, NY (US)

( * ) Notice: Subject to any disclaimer, the term of this patent is extended or adjusted under 35 U.S.C. 154(b) by 780 days.

(21) Appl. No.: 16/326,331

(22) PCT Filed: Aug. 23, 2017

(86) PCT No.: PCT/US2017/048243
§ 371 (c)(1),
(2) Date: Feb. 18, 2019

(87) PCT Pub. No.: WO2018/039366
PCT Pub. Date: Mar. 1, 2018

(65) Prior Publication Data
US 2019/0183097 A1 Jun. 20, 2019

Related U.S. Application Data

(60) Provisional application No. 62/378,522, filed on Aug. 23, 2016.

(51) Int. Cl.
*A01K 29/00* (2006.01)
*A01K 1/03* (2006.01)
(Continued)

(52) U.S. Cl.
CPC ............ *A01K 29/005* (2013.01); *A01K 1/031* (2013.01); *A01K 23/00* (2013.01); *A61B 5/0507* (2013.01);
(Continued)

(58) Field of Classification Search
CPC .... A01K 1/0356; A01K 1/031; A01K 29/005; A01K 1/03; A01K 15/02; A01K 39/0213;
(Continued)

(56) References Cited

U.S. PATENT DOCUMENTS 4,976,220 A * 12/1990 Gershman ................ A01K 7/06
119/475
2004/0143403 A1 * 7/2004 Brandon ................ G16B 25/10
702/19

(Continued)

FOREIGN PATENT DOCUMENTS

| EP | 3005869 A1 | 4/2016 |
| WO | 2010144494 A2 | 12/2010 |
| WO | 2012018756 A2 | 2/2012 |

OTHER PUBLICATIONS

Nov. 6, 2017—International Search Report and Written Opinion—Appl. No. PCT/US2017/048243.
Jan. 14, 2020—(EP) Examination Report—App 17768276.2.

*Primary Examiner* — Jeffrey R Larsen
(74) *Attorney, Agent, or Firm* — Banner & Witcoff, Ltd.

(57) ABSTRACT

A method and system for the continuous monitoring of animal physiology in laboratory animal cages through the use of miniaturized sensors located throughout the cage and in various fashions including the ability to identify each rodent's digital sensory signature through data fusion and artificial intelligence.

15 Claims, 11 Drawing Sheets

(51) Int. Cl.
*A01K 23/00* (2006.01)
*A61B 5/0507* (2021.01)
*A61B 5/11* (2006.01)
*G01S 13/02* (2006.01)
*G01S 13/88* (2006.01)
*A61B 5/00* (2006.01)
*A61B 5/021* (2006.01)
*A61B 5/024* (2006.01)
*A61B 5/20* (2006.01)

(52) U.S. Cl.
CPC ......... *A61B 5/1113* (2013.01); *G01S 13/0209* (2013.01); *G01S 13/88* (2013.01); *A61B 5/021* (2013.01); *A61B 5/02405* (2013.01); *A61B 5/1105* (2013.01); *A61B 5/20* (2013.01); *A61B 5/7221* (2013.01); *A61B 2503/42* (2013.01); *A61B 2560/0252* (2013.01); *A61B 2562/0219* (2013.01); *A61B 2562/08* (2013.01)

(58) Field of Classification Search
CPC ....... A01K 23/00; A61B 5/1113; A61B 5/021; A61B 5/02405; A61B 5/7221; A61B 2503/42
USPC .............................. 119/417, 475, 456, 61.51
See application file for complete search history.

(56) References Cited

U.S. PATENT DOCUMENTS

| | | | |
|---|---|---|---|
| 2008/0306980 A1* | 12/2008 | Brunner | G16B 40/20 |
| 2012/0180731 A1* | 7/2012 | Garner | A01K 1/031 |
| | | | 119/417 |
| 2014/0070958 A1* | 3/2014 | Foo | A61B 5/6892 |
| | | | 340/870.07 |
| 2015/0141794 A1 | 5/2015 | Foo | |
| 2016/0120153 A1* | 5/2016 | Iriki | A01K 1/031 |
| | | | 119/421 |
| 2016/0212971 A1 | 7/2016 | Hill | |
| 2016/0316723 A1* | 11/2016 | Wall | A01K 11/008 |

* cited by examiner

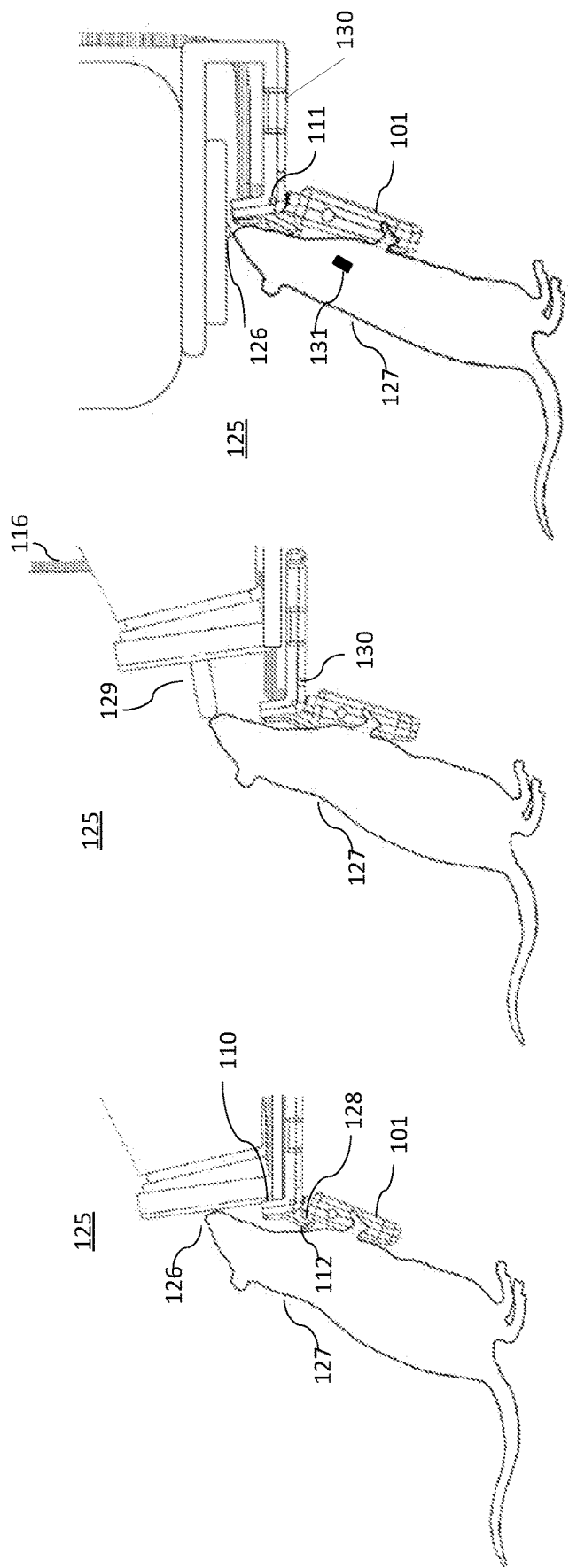

MONITORING AND IDENTIFYING LABORATORY ANIMALS THROUGH UWB AND OTHER DIGITAL SENSORY SIGNATURES

CROSS-REFERENCE TO RELATED APPLICATIONS

This application claims priority to, is a U.S. National Stage application under 35 U.S.C. § 371 of International Application PCT/US2017/048243 (published as WO 2018/039366 A1), filed Aug. 23, 2017, which claims benefit of U.S. Provisional patent application Ser. No. 62/378,522, filed on Aug. 23, 2016, the contents of which are hereby incorporated by reference in their entirety.

TECHNICAL FIELD

One or more aspects of the disclosure relate to the monitoring of animals in a live animal research setting using various sensors including ultra-wideband (UWB) technology in various fashions including the ability to identify cage occupants through their unique digital sensory signatures.

BACKGROUND

Animal monitoring of vital signs in various settings, whether it be in pre-operation, surgical, post-operation recovery, home, clinical, or a laboratory setting, all benefit from the use of monitoring techniques which do not require any physical intervention to obtain valid physiological readings.

The use of hands free automated monitoring systems is preferable to the animals being handled to take such readings as such a method does not disturb the animal, cause any harm, or increase anxiety levels. Automated monitoring techniques will also result in more accurate readings as identified in clinical research papers what has become known as the "white coat syndrome". In terms of invasive RFID implants that may provide core temperature, glucose, and other physiology readings, these types of passive RFID techniques usually require a human-operated/hand-based reader to be present within 3 cm of the actual implant or that the animal has to be put into a separate monitoring container. Research papers show that animals consistently react negatively or positively to the close proximity of humans (even as far as varying based on the sex of the veterinary technician). As such, the monitoring of animals may be influenced by the very act of attempting to obtain the readings. This increase in an animal's anxiety levels or the hiding of pain levels will lead to the capturing of false readings. In a laboratory setting there is continued regulatory pressure to provide an environment that assists in meeting what has become known as the three "R's" principles of Replacement, Refinement, and Reduction as published by W. M. S. Russell and R. L. Burch. If done properly, the capturing of continuous and more reliable clinical information will allow for the development of more accurate animal computer models and therefore lead to a replacement of laboratory animals where computer models will now suffice. Refinement may be achieved if the automated monitoring environment enhances an animal's well-being and minimizes or eliminates unnecessary pain or distress. Reduction may be achieved if the amount of information gathered may be maximized from a given number of animals so that in the long run, fewer animals are needed to acquire the same scientific information.

Although the use of RFID implants helps in addressing some of the negative aspects of animal handling and their effect on clinical data accuracy, as described above, it is expensive and inconvenient to have technicians approach the animals with RFID wands or place them in temporary RFID reading enclosures.

Rodentia, in a live animal research sitting, may also be placed in temporary enclosures to measure their physiology by measuring the animal's electrical currents as detected through their feet or skin, using a pressure cuff around the tail area, or using photoplethysmography (PPG) on a limb or at the base of the tail. In all cases, the animals have to be physically moved from their base cage to a special temporary cage/container with metal electrodes on the bottom, or put into special animal restraint holders that use various technologies to take readings from their tail, feet, or thigh with a clamp. After taking such readings taken in this fashion, the animals have to be returned to their home cage and the monitoring equipment disinfected for the next batch of test subjects. The above mentioned work flow is both cost prohibitive from a labor and a capital standpoint. Due to these factors laboratories have a difficult time meeting the standards as outlined in the "R's" as the monitoring solutions cannot be economically propagated across the entire laboratory setting.

SUMMARY

To address the above issues, the deployment of miniaturized electronic devices is disclosed such that they may be attached to or placed in existing rodentia cages that are in use today in laboratories by various methods and left unattended for continuous monitoring. Technologies employed would include, but not limited to, UWB, mm-wave, IR, ultrasonic, capacitive sensing, RFID, bio-impedance, micro electromagnetic fields (EMF), piezo, passive miniature wireless pressure sensors, positron emission tomography (PET), moisture sensors, and urine and bio-marker analysis sensors, etc. Such a system is designed to be deployed at fraction of the cost of the current solutions in the marketplace to allow for scalability to the entire laboratory population without the associated labor overhead per animal.

In one embodiment, a small self-contained paddle is attached under each water delivery system in the cage. Inside of the paddle is a matched pair of ceramic UWB antennas, a control PCB incorporating a microcontroller, memory, and additional sensors such as a 6-axis accelerometer and one or more radios such as LoRA, WiFi and Bluetooth. In other embodiments, only the UWB antenna, accelerometer, and temperature sensors are located in the paddle and the control electronics are located in a central electronics enclosure located at the top of the cage (or bottom of the cage on a side or even on the back of the cage) with a much larger support battery. Such a central control electronics enclosure would also be able to service multiple UWB paddles or like sensors located in the cage. In yet in another embodiment, the cage itself would be situated in a rack that would hold many cages. In this case, the paddles themselves would be connected through an armored cabled (or coax or optical cable) to a small electronic switch on top of the cage. The switch in turn would be networked to a harness that runs along the back of rack across each row of cages. These connections would in turn be connected to a central rack hub on top of the rack itself. This central rack hub would provide power to each of the paddles through the cage top switches, as well as interact with the paddles on a two-way basis to send instructions to the paddles as well as gather the monitoring data. The central rack hub may also monitor, through on-board sensors, various ambient conditions such rack humidity, temperature, light, and rack resonant frequency etc.

Whether UWB or other technologies as described above are employed in the rack, which may include dozens of other cages and multiple racks of cages, there is the chance of signal leakage, interference, or conflict with regulatory bodies such as FCC on radio emissions levels. This is further compounded by the fact that there may also be several data transmission radios on board associated with each sensor pod as well. To address these issues, there are several mitigation strategies available which include on-board algorithms to monitor and schedule physiological signal acquisition and data transmission per unit, rack location (i.e., where a given cage is located in a rack of cages)-based algorithms to manage all the cages in a specific rack and room-based algorithms that are controlled by the central server-based analytical system (including but not limited to selectively activating the sensors in one or more cages to determine which sensors of which cages interfere with each other and then schedule—or operate—such that they signals from the cages do not interfere with each other). Techniques could include dithering so that sensors do not fire all at the same time, frequency hopping of transmission channels, and adjustments to the transmission power of the radios. In the case of UWB-based sensors, each individual sensor transmission may include an electronic serial number of the specific sensor transmitting so that even if there was leakage into another receiving sensor's circuitry, the received signal would be ignored. In the case of individual self-contained paddles, which are not centrally controlled, radio transmission mitigation strategies may include using various techniques as described above except some of them would be administered by the technician directly or by on-board algorithms in their mobile tablet device as the technician is adding, removing, initializing, or decommissioning cage-based sensors. The self-contained paddles would also have sensors on-board to monitor the environment that they are operating in to cease certain types of transmissions if they detect a potential conflicting signal and to schedule and prioritize data transmissions based on radio "quiet" times or based on the importance of the data they are holding.

The paddle is attached to the cage through attachment methods that will fit the various cage manufacture's designs and water delivery systems whether it be plastic, wire or a combination of the two. Such attachment strategies could include using a type of strong elastic bands similar to what is used in human dental appliances, using vice or compression types of connectors or through the use of suction cups attached to the top, bottom or sides of the cage.

In one embodiment, to obtain vital sign readings, the rodent while drinking, leans against the paddle triggering the device to turn on. The UWB and other types of on-board sensors record a time stamped heart rate, respiration rate, relative blood pressure, and resonate frequency of the animal. Such readings may be obtained by detecting the micro movements of the heart muscles, blood vessels, and chest muscles. As a by-product of the UWB's sensing capability it would also provide an indication of a buildup of fluids in the animal's lungs and/or around its heart as well as a derived heart rate variability (HRV) indicator.

The captured data is then spot checked for reasonability and accuracy using on-board algorithms before being stored temporally in the main memory of the paddle device, stored in the top of the cage located control electronics enclosure or stored in central rack-based hub. Such data is then augmented with additional sensor data that may been collected from external sensors along the way such as various RFID implant readings, ambient temperature readings, ambient humidity readings, ambient light readings, and the ambient resonant frequency of the cage system. Paddle sensor activations may also be used to trigger external or internal video-based systems that may be used to monitor the animal's behavior and/or be used to help identify which animal triggered the sensor array monitoring system. The video system could be in the form a small camera with special filters and capabilities that is placed in the cage over the water delivery system and attached to the top of the cage electronics enclosure. Not only could this camera be used for animal identification by using advanced face recognition software or by reading the ear tag ID markings but it may also be used to measure pain or wellness levels using the image-based rodent grimace scale. Other techniques could include the monitoring of heart rate through image-based PPG technology looking at the minute color changes in the capillaries in the animals face and nose, looking at precursors of diabetes by examining the retina of the animal using diabetic retinopathy and/or identifying the animal by looking at the unique retinal blood vessel pattern of the eyes or the unique resonant frequency pattern of the animal's whiskers.

The base paddle obtained data and augmented data is then transmitted to the local server or the cloud by Ethernet cable, WiFi, Bluetooth, cellular, UWB, LoRA, or other types RF technologies.

Once the data is at site of the central analytical system it is first scrubbed for accuracy, then coefficients are applied and the fused data goes into the deep learning engine where it is matched against a validated pre-known set of parameters to determine which rodent to assign the acquired sensory data to all based on their unique digital sensory signature. In any case, if the readings are outside a set of preset normal values, an alarm will be triggered that may be communicated by various methods including email, text, flashing the monitor screen and/or flashing LED's at the cage paddle level and cage control unit level which may be picked up by authorized personnel.

In another embodiment the UWB technology is replaced or supplemented with other technologies such as ultrasound, mm-wave, bio-impedance, EFM, capacitive sensing, strain gauges, and RFID implants, etc.

In another embodiment, all of the technologies described above may be employed in combination with a common plastic or cardboard rodent retreat (this is where the animal goes for quiet time) usually placed on the floor of the cage. Such an employment of the various technologies may provide important animal physiological readings as well other cage-based measurements such as moisture (waste) levels, urine/waste analysis, biomarker analysis or the detection of water delivery system failures. Proximity sensors are used to detect the presence of a rodent in the rodent retreat and then various technologies as described above may be triggered to capture various physiological signs. Such readings may be transferred to data collection points at the cage, rack or room level using technology as described previously associated with the paddle-based sensor by wireless techniques or directly by armored cable.

In another embodiment, all of the electronics and sensors are located in a smart pad that fits either in the bottom of the cage underneath the bedding or fits underneath the cage situated between the bottom of the plastic cage and the rack that is holding the cage in place. If the pad is placed on the floor of the cage, like the rodent retreat as described above, the sensors on the underside of the smart pad have the opportunity to sense and analyze the fluids that collect below the pad including looking for biomarkers with various spectrum analysis or chemical reaction-based sensors. As the cage pad covers the entire surface of the bottom of the cage there is an opportunity to count the number of occupants in the cage and track their movement using the UWB technology as well as measuring heart rate, respiration and blood pressure for each individual animal. These movement artifacts may be valuable to the researcher or the veterinary technician to know when a rodent has had a litter or if one of the occupants has deceased as well as measuring activity and behavior.

The animals in question may have RFID implants in them, which among other things may include the ID of the animal. By placing RFID readers around the perimeter of the cage and at important cage locations such drinking, eating, resting, and elimination etc. various behavioral readings may be captured and eventually transmitted to the central analytical system.

To measure water consumption and food consumption, small passive RFID strain gauges or other technologies may be placed under where the water bottle sits against the cage and under a pressure plate that the food is loaded on. When the RFID strain gauge is excited by various radio sensors located in the cage, the resulting data would be transmitted and added to the central analytical server for reporting.

BRIEF DESCRIPTION OF THE DRAWINGS

FIGS. 3A-3C show illustrative examples of rodents being sensed when drinking or feeding in accordance with one or more aspects of the disclosure.

DETAILED DESCRIPTION

Figure 1:
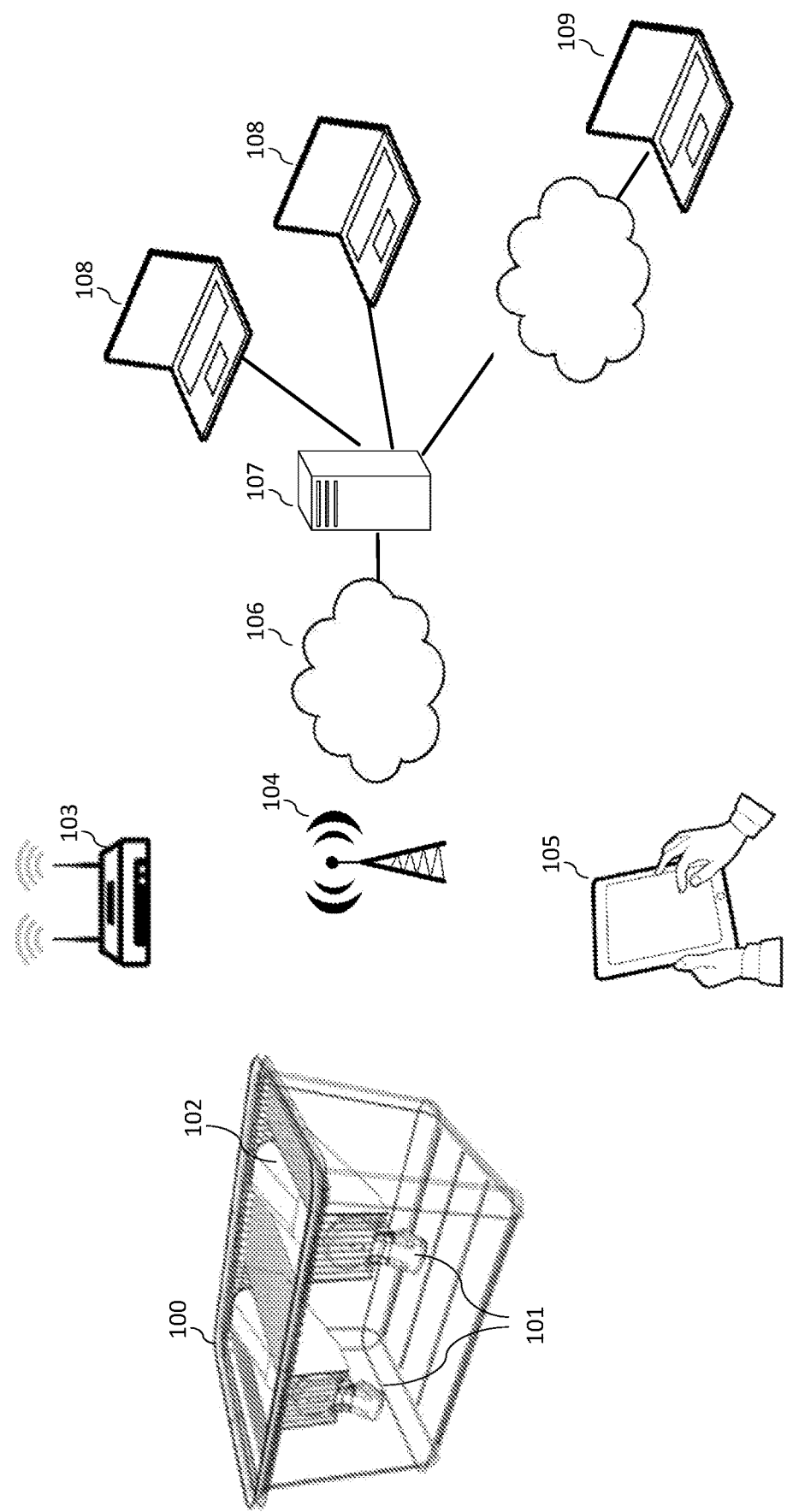
FIG. 1 shows a rodent cage in a laboratory in accordance with one or more aspects of the disclosure.

FIG. 1 shows a rodent cage 100 in laboratory setting that includes two UWB paddles 101 attached to the cage below the water delivery system 102 (possibly including a spigot or tube as known in conventional water delivery systems). In this particular depiction, the paddles 101 have a complete makeup of a microcontroller, sensors, battery, radios and various antennas. Therefore, it may act independently on its own or communicate interactively by various RF techniques such as Wi-Fi 103, cellular, UWB, LoRA, or other RF techniques 104, and/or through Bluetooth to a nearby laboratory technician with a tablet or other type of mobile device 105. Having the tablet close by while setting up the cage with the various occupants would be useful in obtaining confirmation of each rodent as they drink from the water delivery system for the 1st time. This event may be correlated with the obtained digital sensory data to provide a unique digital finger print of each animal back at central analytical system 107. Such raw, augmented and processed data may then be accessed by knowledge workers 108 located either onsite 109 or remotely located to the central analytical system.

Figure 2C:
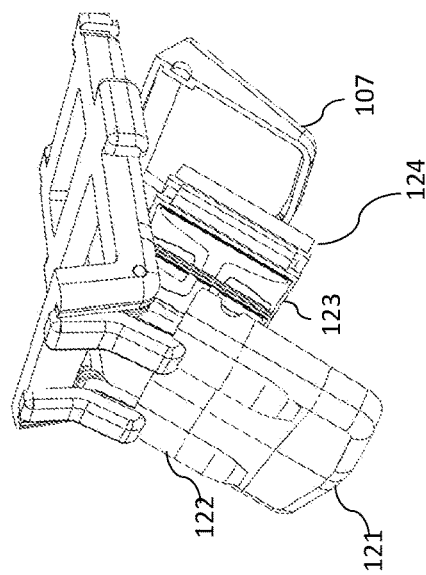
FIGS. 2A-2C show various paddles in accordance with one or more aspects of the disclosure.
Figure 2B:
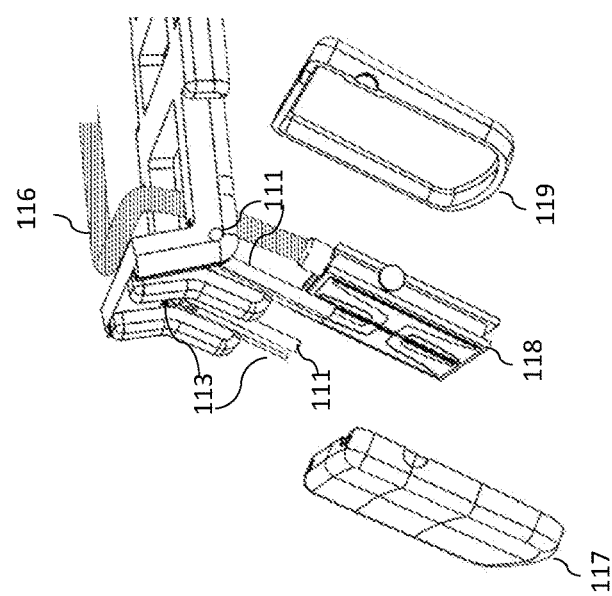
Figure 2A:
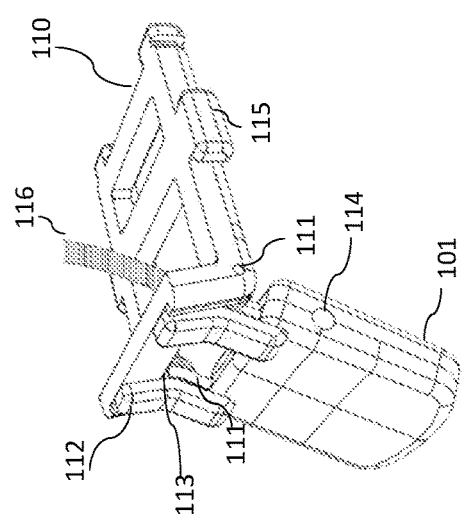

FIG. 2A shows a detailed view of a paddle version that only includes the UWB antennas, the UWB control circuitry and other sensors such as a 6 axis accelerometer and activation sensors of various types. The UWB paddle 101 depicted here is free moving in that it is attached to the cage adapter bracket 110 by a pin 111 and is pushed against the paddle stopper 112 by the spring 113. When the rodent leans up against the paddle 101 it pushes the paddle backwards while the rodent makes full body contact with the paddle. The presence of the animal may be detected by a mercury switch, the on-board accelerometer, or a proximity sensor to determine that a qualified event is taking place. The UWB sensor or other comparable technology is then triggered to capture various physiological readings. To indicate that a successful reading is taking place, the LED 114 on the side of the paddle changes color.

The cage adapter 110 may be attached to the rodent cage in various ways. In FIG. 2A there is a depiction of small wings 115 attached to the side of the bracket where strong elastic bands may be attached to one side of the adapter and then threaded through the wire cage over to the other side. This design does not require a cage wire mesh of any particular dimension or spacing. In this particular embodiment the UWB paddles 101 communicate to a top of cage central electronics controller through an armored cable 116.

In FIG. 2B an exploded view of the paddle 101 is depicted with the top cover 117, the electronics and antenna package 118, and the back cover 119 shown. Also shown is the armored cable 116 that connects directly to the paddle electronics package 118. Also shown is the stopping bracket 113 and the two "L" shaped downward facing pins 111 that are used to hold the paddle 101 and springs 113 in place. As indicated, the springs 113 have both an upper coiled position and extended straight long position that also inserts into the paddle just like the "L" shaped pins 111. Included in the electronics package 118 are a matched set of UWB ceramic antennas for RX and TX functions that are either angled or situated on a flat plane. The onboard 6 axis accelerometer may also be used to take the resonant frequency of the rodent as it leans into the paddle as well as obtaining an ambient background resonant facility frequency readings once the paddle returns to its resting position. Such readings may also be used by the UWB algorithms to reject various readings or to re-calibrate the UWB frequency domain filters to better isolate the desired rodent UWB signals.

In FIG. 2C there is side view representation of the exploded view of the paddles 101 that is different from what is depicted in FIG. 2B. In FIG. 2C, the front of the paddle 121, is slightly curved and has two small protrusions 122 on it which allow the UWB antenna's 123 to be angled to better obtain UWB readings as well as channel the rodent into the center of the paddle's 121 front housing. This is in comparison to FIG. 2C where the antennas 118 are on flat plane. In this embodiment of the UWB paddle 101, the unit is totally self-contained in that it includes all of the hardware and software components to operate and communicate independently including its own battery 124. As most short term toxicology studies are no longer than three weeks in length, this design would suit study protocols where the researcher has instructed the laboratory that no external wires of other electronic enclosures are to be present in the cage.

In FIGS. 3A-3C, depicted are examples of how the stock UWB paddle 101 may be adapted to the various cage styles and water delivery systems. In FIG. 3A the water delivery system 125 is at a 45° angle with a flat nipple 126 and the cage adapter 110 is snug up against side of the cage and water bottle 125. In this case the rodent 127 displaces the paddle 101 producing a gap 128 between the paddle 101 and the stopping bracket 112 and the electronic readings commence.

FIG. 3B is identical to FIG. 3A except that the flat nipple 126 has been replaced with an extension spout 129. To accommodate this arrangement, the standard cage attachment system is replaced with an extension cage attachment bracket 130 which extends the paddles 101 out further to interact with the rodent 127. In another embodiment, the cage attachment bracket also has an upright protrusion located further along the bracket 130 with a hole in it which allows the spout 129 to pass through it and therefore providing more support for the entire assembly.

In FIG. 3C the water delivery systems are at a 90° angle with a flat nipple 126. In this case a different cage attachment bracket 130 is used that sits around the opening for the water delivery system 125 and then extends out and down to where the paddle 101 may be attached with the retaining pin 111. Usually these types of water delivery systems 125 allow the rodents 127 to approach the flat nipple 126 from any angle. With this embodiment, the paddle 101 is positioned just aft of the flat nipple so that the rodent 127 may only drink from one side which activates the paddle 101 by deflecting it. In another embodiment, the cage attachment bracket 130 is designed to swivel around the water delivery system 125 opening so that the rodents may drink from any angle by just pushing the paddle 101 around to a position that suits them.

FIG. 3C shows the paddle sensory array reading passive or active RFID chips 131 located inside the animal itself. RFID readers may also be located around various perimeter positions as well as situated under the drinking and eating stations. Various physiological readings may be obtained such as glucose levels, core temperature, EMG, EEG, HR, respiration, bio-markers, and pressures in the brain and body etc.

Figure 4B:
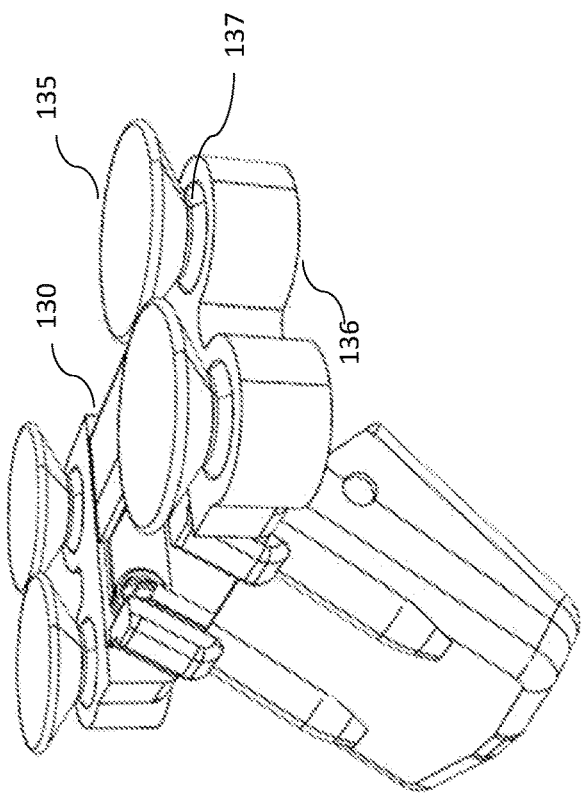
FIGS. 4A-4B show different configurations of paddles in accordance with one or more aspects of the disclosure.
Figure 4A:
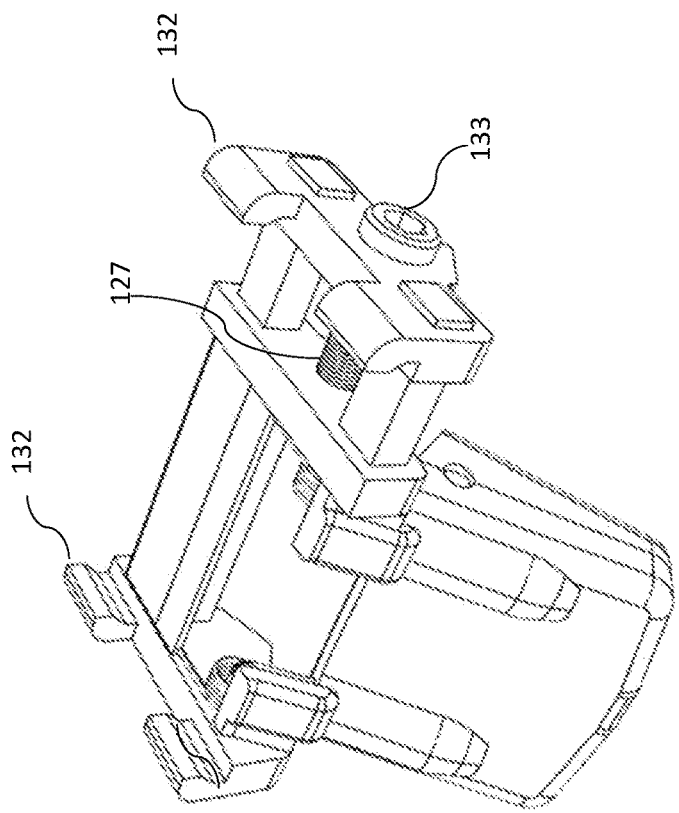
Figure 5A:
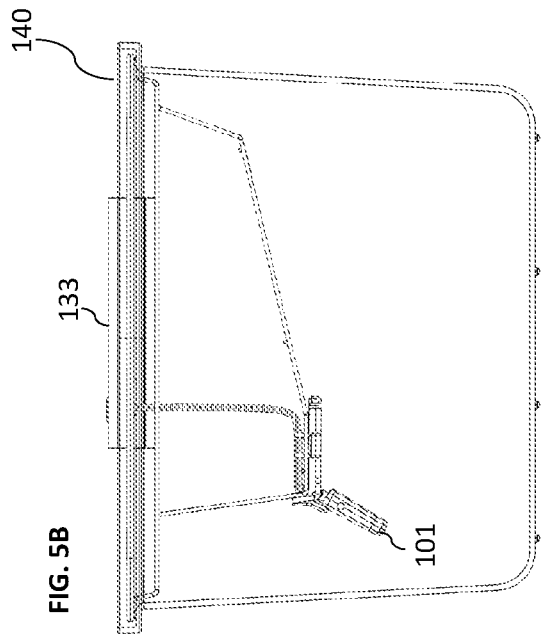
FIGS. 5A-5D and 6 show various enclosures with one or more paddles in accordance with one or more aspects of the disclosure.
Figure 5B:
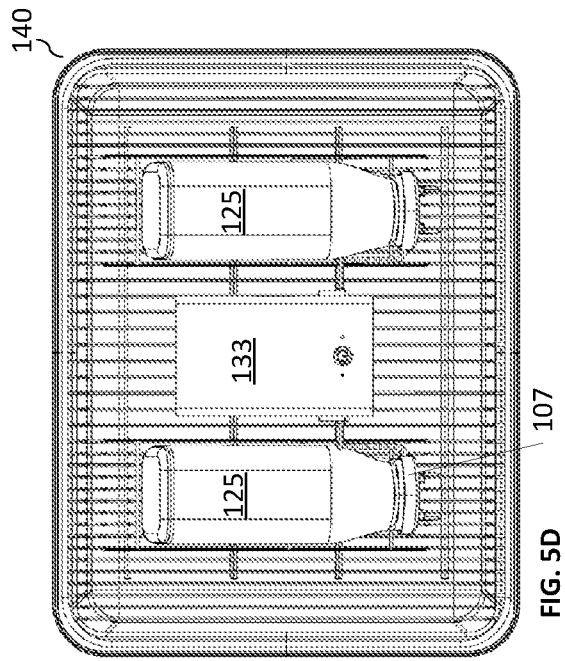
Figure 5C:
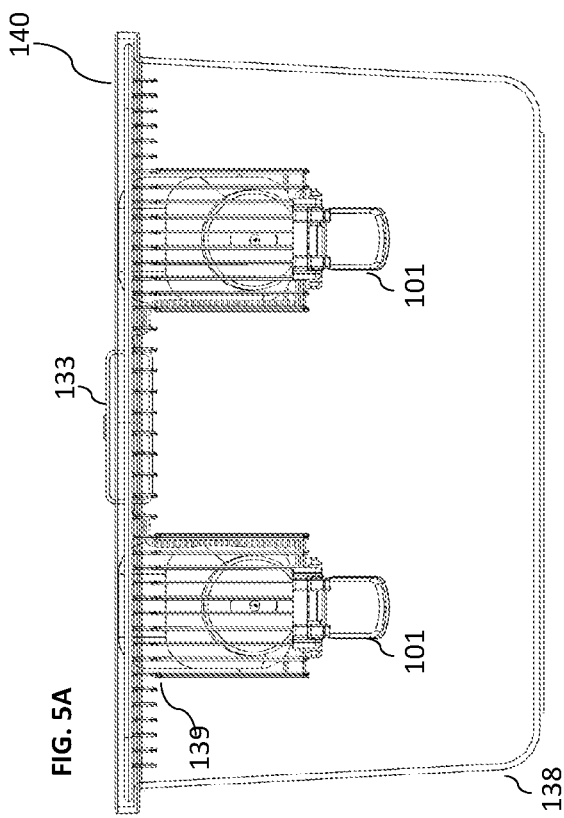
Figure 5D:
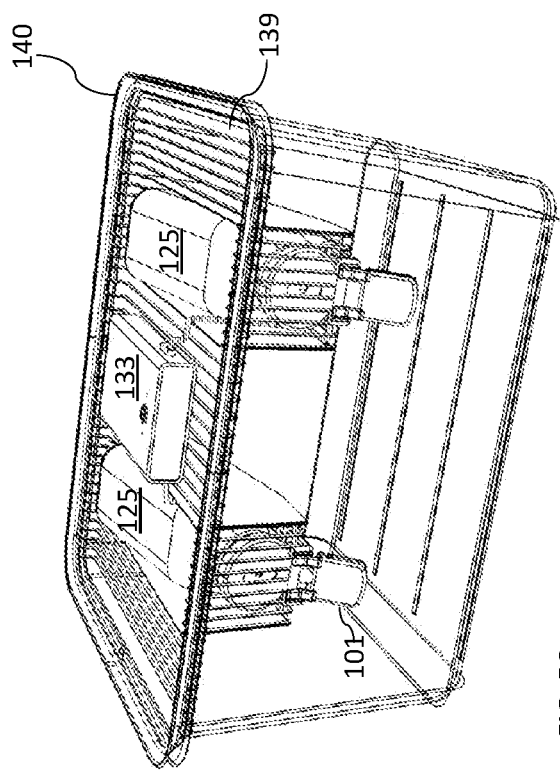

In FIG. 4A, the opposing wings 132 of the adapter are not fixed but moveable and they may be adjusted to grab the wire cage, of any dimension or spacing, in a vice like fashion by using an Allen key placed in the socket 133 of a threated bolt 134 to compress or expand the wings 132 position relative to each other.

FIG. 4B shows an example for an all-plastic cage top. In this case, the adapter 130 uses suction cups 135 attached to the wings 136 of the UWB paddle cage attachment which will in turn attach to the underside of the plastic cage top, bottom, side of the plastic cage. The mounts that the suction cups are on also swivel 137 as well as they may be designed to extend or retract the suction cups 135 to allow for flexibility in attaching to various surface shapes other than just flat surfaces.

FIG. 5A, 5B, 5C, and 5D show different views of one version of the rodentia electronic cage system which includes a lower unit 138, the top unit 139 that holds the food and water system, the top lid 140 the UWB paddles 101, the water delivery system 125 the connecting armored cables 116 and the top mounted cage control electronic enclosure 141. The top mounted control electronic enclosure may also contain RFID antennas for interrogating implants inside the animal as well communicating with other types of external RFID sensors. These types of external sensors could include flat microchips that measure the amount of moisture or liquid in the bottom of the cage and/or analyze the actual urine for specific bio-markers. Such data collected could assist in identifying which cages need cleaning attention and/or provide valuable research data.

Figure 6:
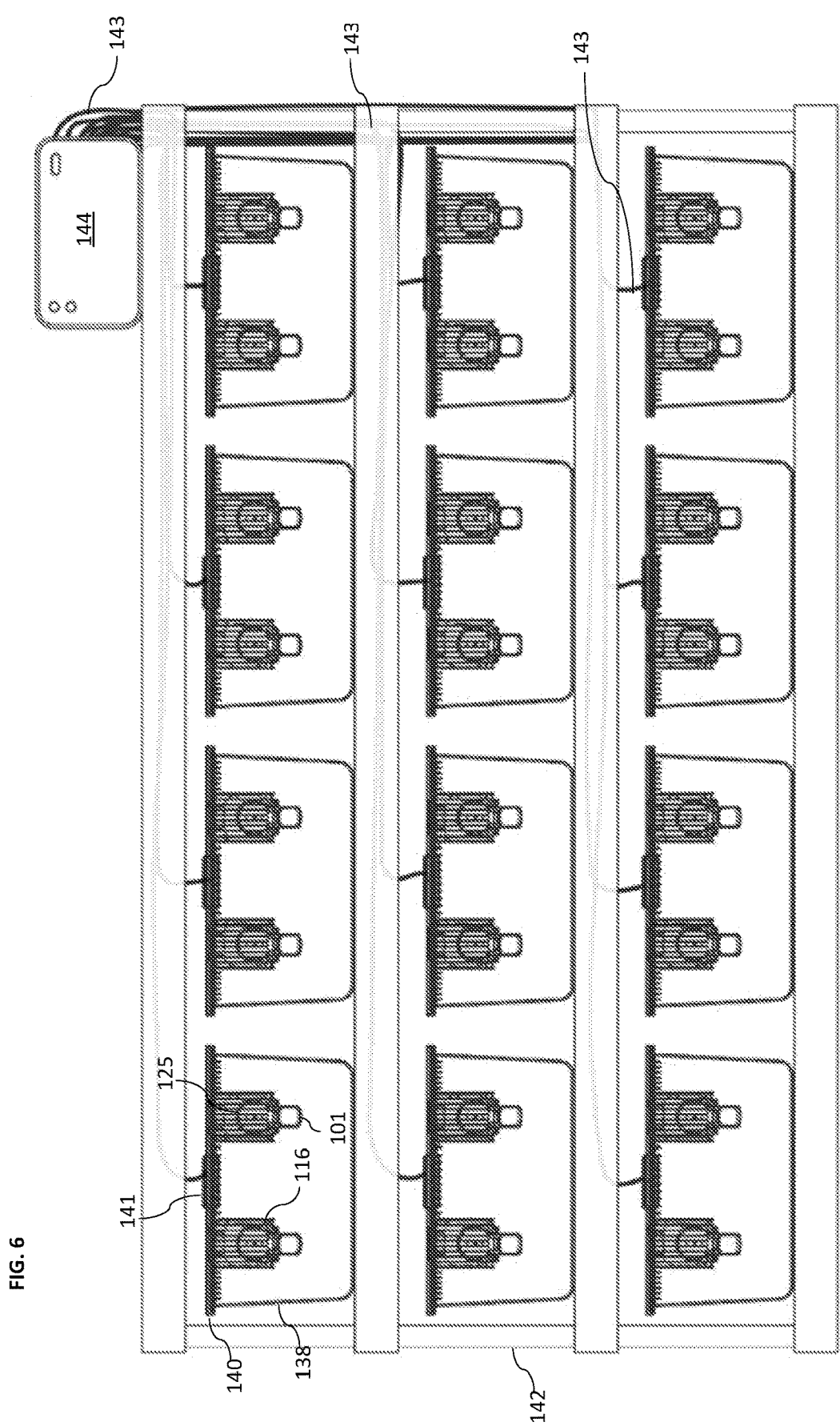

In FIG. 6 what is depicted is a rack 142 that holds several cages with bottoms 138, tops 140, water delivery systems 125 and UWB paddles 101. In this embodiment the paddles 101 connect through the cables 116 to a small switch 141 that is located on top of the cage top 140. This switch in turn is attached to a wiring harness 143 that runs along the back of the rack 142 up to a central rack control box 144. The rack control box includes a power management system for supplying power to all of the cages in the rack. It also provides a central place to store all data collected from the paddles 101 and as well as other sensors that are part of the overall system, such as humidity, light levels, RFID readings, and motion artifacts etc., wherever they may be located. The central rack control box also provides various ways to communicate to the local or in cloud analytical system 107 such using Ethernet cables, Wi-Fi, LoRA, Bluetooth, cellular or other RF technologies etc.

Figure 7:
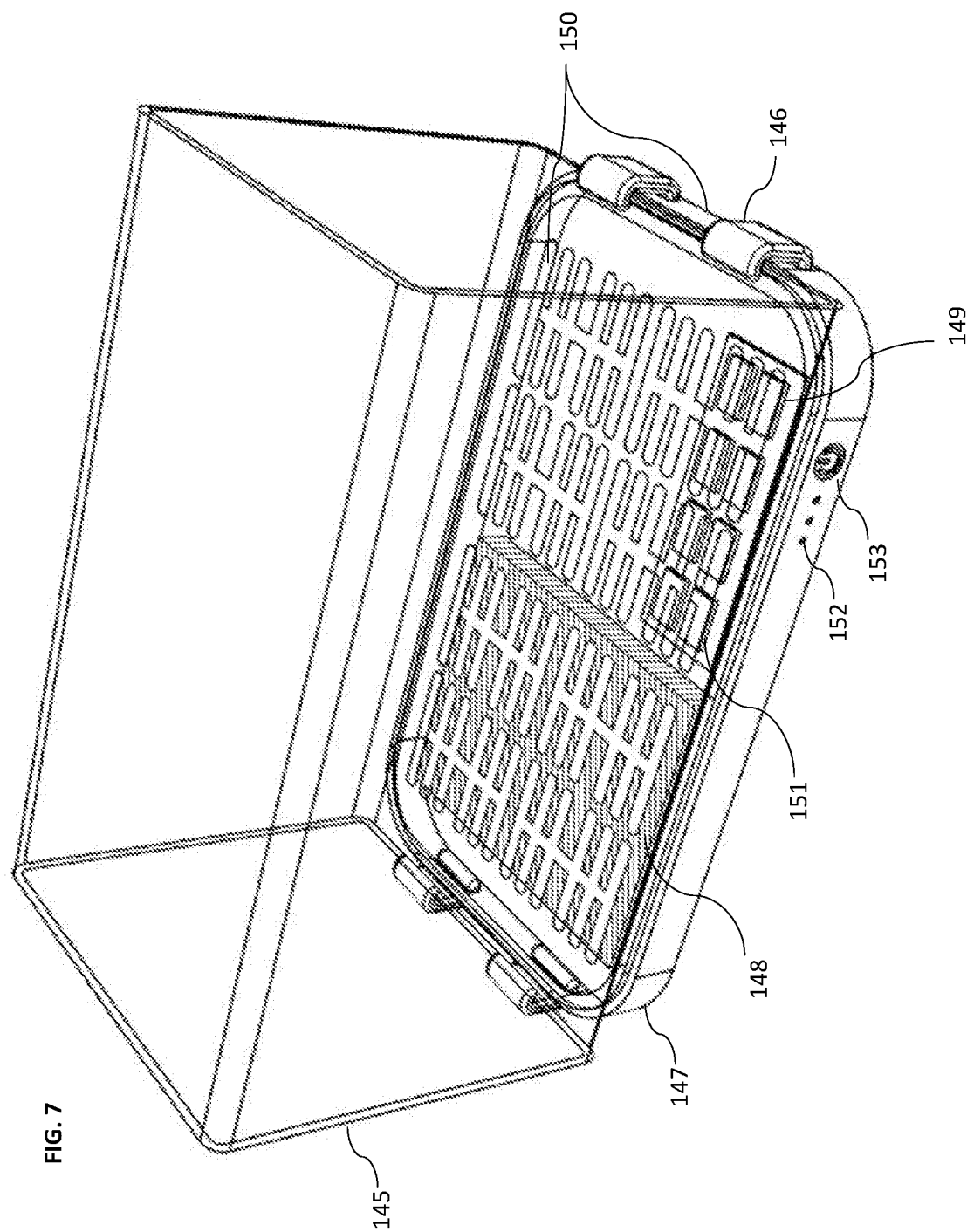
FIGS. 7 and 8A-8B show alternative sensing systems in accordance with one or more aspects of the disclosure.

FIG. 7 depicts an alternative way in the cage 138 to employ sensors of various technologies, such as UWB. In this embodiment, a typical plastic rodent retreat house with enclosure 145 is placed in the cage. The enclosure may be transparent, translucent, or opaque. It may also have various tints—if any—clear, blue, red, yellow, and the like. The enclosure may have various cross sections including square, rectangle, circular, oval, and may be combinations thereof (e.g., a square cross section with rounded corners). Attached to the plastic housing by clips 146 or other means, is an electronics enclosure 147. In another embodiment the electronic enclosure actually sits inside the plastic enclosure and not attached to the bottom. Regardless of its position, the enclosure includes a PCB containing a micro-computer, memory, a battery 148, proximity sensors and radio antennas 149. Physiological sensors, including RFID readers 150, are located both on the top of the electronics enclosure and on the bottom of the enclosure. There are also radio transmission antennas 151, LED indicators 152 and an on/off switch 153. As the animal enters the enclosure 145, a proximity sensor 149 activates the sensors 150 and starts the monitoring process. In another embodiment, the actual electronics pad may be designed and manufactured to be much thinner as the bulky electronic items such as the battery, LED's and switches 148, 152, 153 etc., may be moved to the side or the end of the unit in a form of a tab. Data from this type of design may be transferred to the central analytical system 107 using various on-board radio technologies or by an armored cable attached to a switch 141 on the top of the cage. All previously mentioned techniques for managing sensor data as described above at the cage, rack, or room level are also applicable.

Figure 8B:
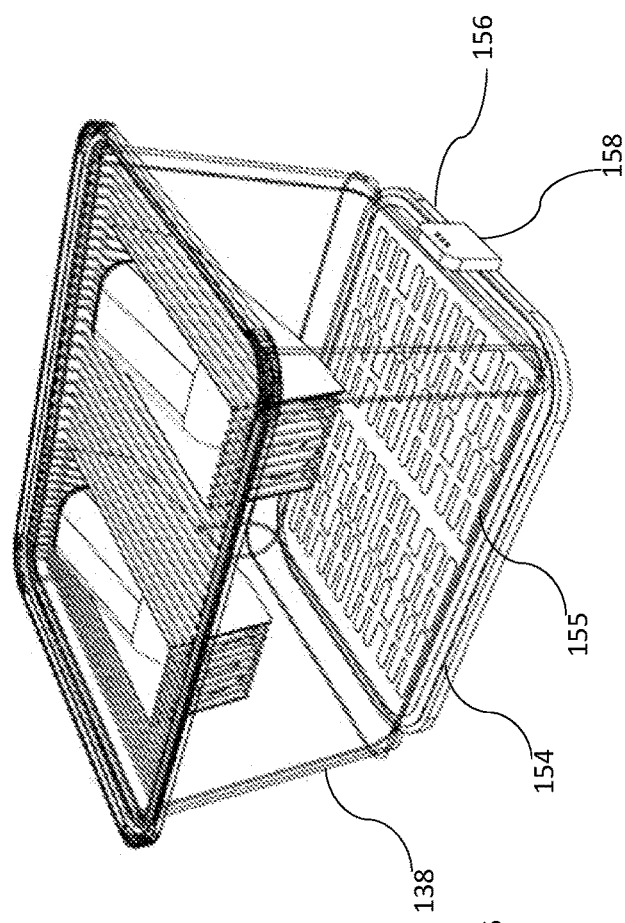
Figure 8A:
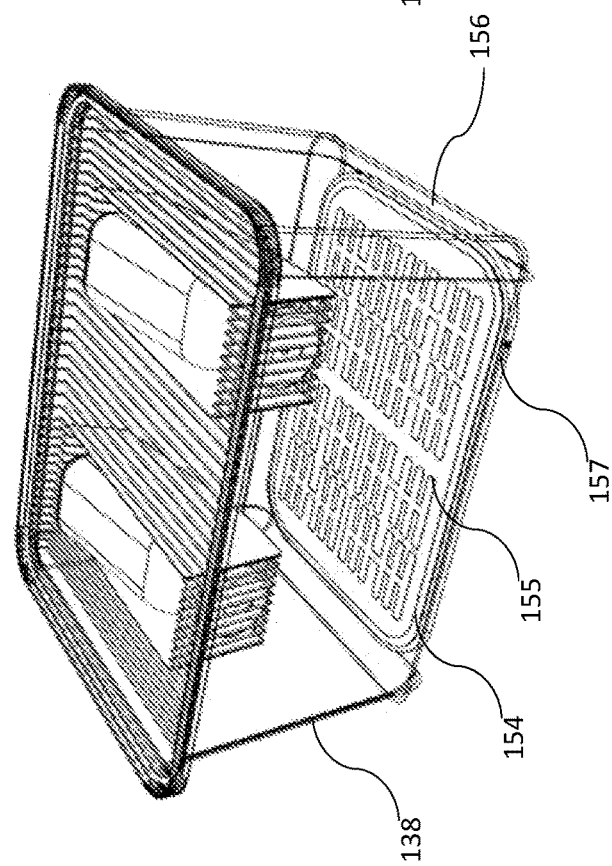

In FIG. 8 there is a depiction of a smart cage-based pad in two different versions. FIG. 8A depicts a typical rodent cage 138 where the smart cage pad 154 is situated on the bottom of the cage. The pad has an array of sensors 155, including UWB sensors, located on the top of the pad and other sensors located on the bottom of the pad 156. The pad has area designated to provide a user interface 157 in the form of LED's and a switch in this example. This user interface may be situated on the side of the pad as depicted here or it may be on the end facing out for veterinary technicians to review similar to what is depicted in FIG. 8B. In FIG. 8B, there is a depiction of a smart cage pad that is placed under the cage 138 bottom between the cage bottom and the top a racking system that holds many cages (not shown here). In this depiction, the user interface as described in 8A is replaced with an electronics tab 158. This tab may hold bulky electronic items such as the battery, LED's switches etc., allowing the pad to be much thinner. The increased size of the electronics tab allows for the inclusion of a display screen (not shown) versus just relying on LED's to convey important operational status information of the smart pad. Regardless of location, the smart pad may perform all of the operations of the rodent retreat pad as described in FIG. 7, except the when the pad in placed under the cage bottom it of course does not have direct access to the waste material therefore it would have to rely on other technologies on the top side of the sensor array to perform analysis of the waste material and liquids. In either case, as the cage pad covers the entire surface of the bottom of the cage there is an opportunity to count the number of occupants in the cage and track their movement using the UWB technology as well as measuring heart rate, respiration and blood pressure for each individual animal. Either of depictions shown they may also be connected directly to cage-based or rack-based external power supplies and communications modules by an armored cable (not shown).

Figure 9:
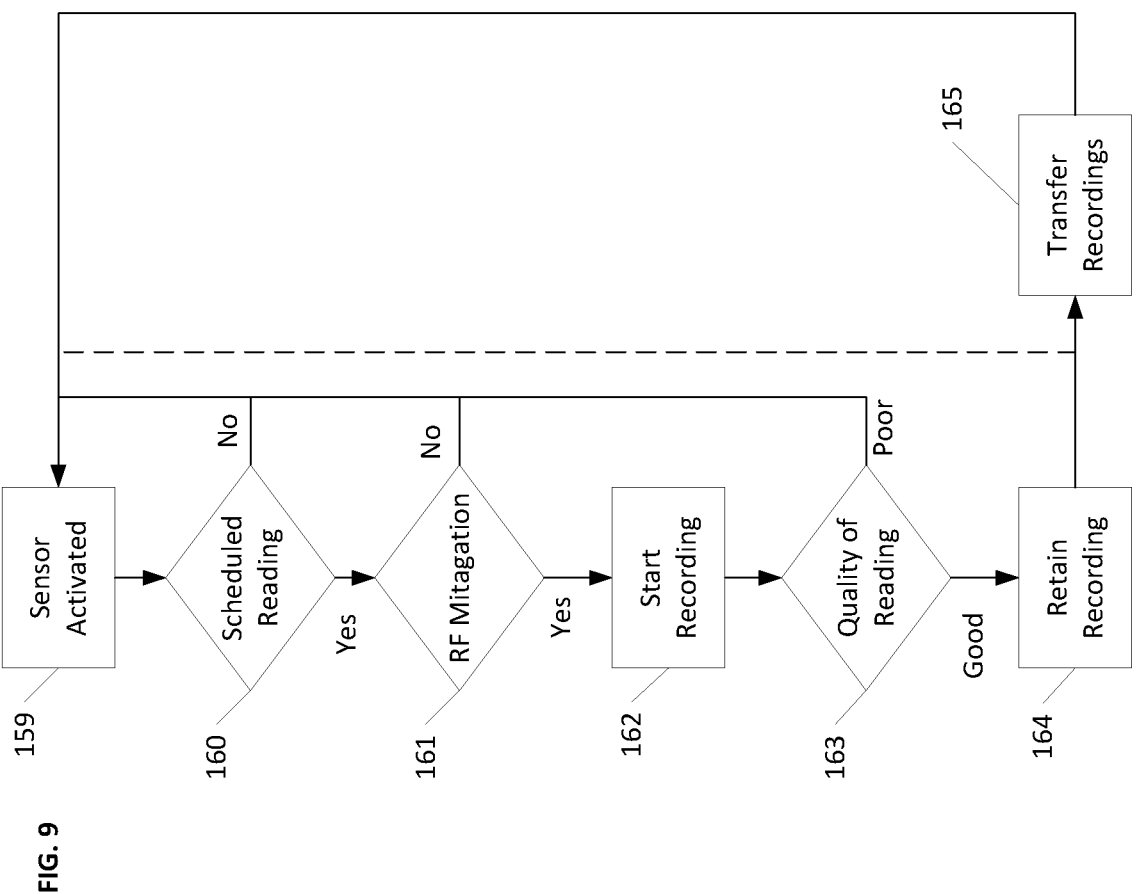
FIG. 9 shows a sensor reading sequence in accordance with one or more aspects of the disclosure.

FIG. 9 shows a flow chart of the sensor reading sequence that may be used on various embodiments described herein. Once the UWB paddle sensor 101, the electronic rodentia retreat 147 or the smart electronic cage pad 154 has been activated 159, by either the animal triggering the on-board accelerometer, mercury switch or proximity switch etc., it checks 160 see if a reading is scheduled. If so, the system then performs mitigation strategies 161 to see if there are any conflicting RF signals inside the electronic enclosure itself, at the cage level, at the rack level, or at the room level. If all is clear, the sensors in the paddles, retreat pad, smart cage pad begins and/or suspends its UWB sensing or RF communicating sequence 159. If a reading is not scheduled, the sensors return to a resting state 159. Once the UWB reading sequence is finished, the quality of the reading is analyzed locally 163 to determine if there were any gross noise artifacts that would disrupt the reading process such as the paddle 101 not being displaced totally or that the duration of the reading was too short etc. In the case of error conditions, the counter would not be incremented and the sensors would return to a resting state 159. If the readings were deemed successful, the readings would then be stored locally 164 and made available for the next scheduled data transmission 165 and the paddle returned to the resting state 159.

Figure 10:
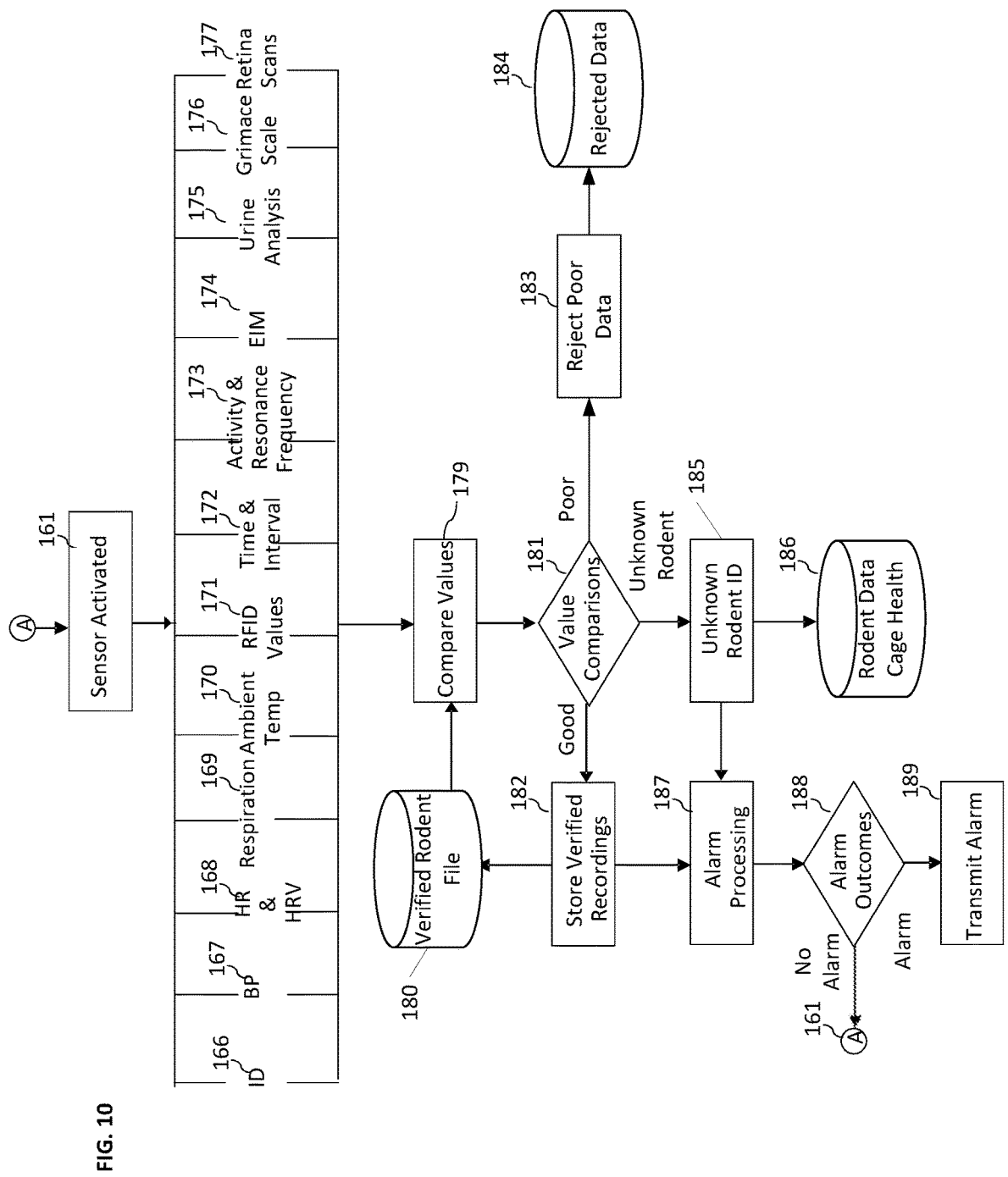
FIG. 10 shows a process for determining which animals have been sensed by the sensors in accordance with one or more aspects of the disclosure.

FIG. 10 depicts the logic work flow for determining what possible readings could be obtained by the sensors when they are activated and by which animal 159. In this case the data from all sensors and sources connected to the system is available to the central analytical system 107. As well as the facility, rack and cage number, this may include animal ID 166 as obtained through RFID implants or video analysis (ear tag etc.), blood pressure 167 HR and HRV readings 168, respiration readings 169, ambient facility/rack/cage temperature 170, core temperature, glucose levels, and pressures levels within the animals' body and brain 171 as recorded through RFID implants, image-based sensors and/or infrared (IR) sensors located on the paddles, the electronic rodentia retreat pad, or the smart cage pad, the time of the encounter 172, resonant frequencies and activity levels of the animal 173 and the ambient resonant frequencies of the cage itself.

In another embodiment, additional readings may be obtained at the paddle level with the addition of two metal contacts which may be designed to make contact with the rodent's front paws as they lean up to drink. Once contact is made, a small electrical current may be passed through one paw to the other paw and electrical impedance myography (EIM) signals may be obtained to derive the animal's body composition 174. Such a reading is more than likely to be unique in comparison to the other cage occupants and therefore provides yet another variable to assist in deriving a unique digital signature per cage rodent.

In another embodiment, small external RFID moisture, urine and other bio-marker waste material analysis sensors 175 may be placed in the bottom of the cage or on the bottom of the rodentia retreat's electronic pad or the smart cage pad that may provide insight into various reactions that the rodents are having to the protocol or to indicate a leak/flood in the water delivery system.

As mentioned previously, another embodiment is the inclusion of a small video camera attached to the cage that is operated externally or connected by various means to the top of the cage central electronic enclosure 144. Not only could this image-based analysis provide possible ID's of which rodents at which time were being monitored, but they could also provide important clinical indicators based on the grimace scale (GS) 176 to monitor pain levels. Another aspect of video analysis is using retina scanning looking for early signs of diabetic retinopathy as well as using the unique vein pattern of the retina for animal identification purposes 177.

All of these values are compared 179 on a raw data basis and on a data fusion basis to all prior confirmed readings located in the verified history database 180. If the readings 181 provide a high enough confidence factor that they match a specific rodent, they are then transferred 182 to the verified history file 180. If the readings look like total outliers, then they are dumped 183 into the reject data file 184. For valid but unknown animal readings they are marked as such 185 and recorded in the composite cage health file 186. In both the known and unknown rodent readings, instances of the data are also sent to the alarm processing module 187 which is used to determine whether 188 an alarm should be raised and sent out by various electronic or display methods 189 otherwise no alarm is sent 161. Alarms may also be based on water, food, or waste levels being monitored.

Periodically all three files will be re-analyzed as new data becomes available, from the sensors or from the direct observational methods, looking for better ways to derive individual digital signatures of each animal and to re-assign data from one category to another, if necessary, using the deep learning engine.

Figure 11:
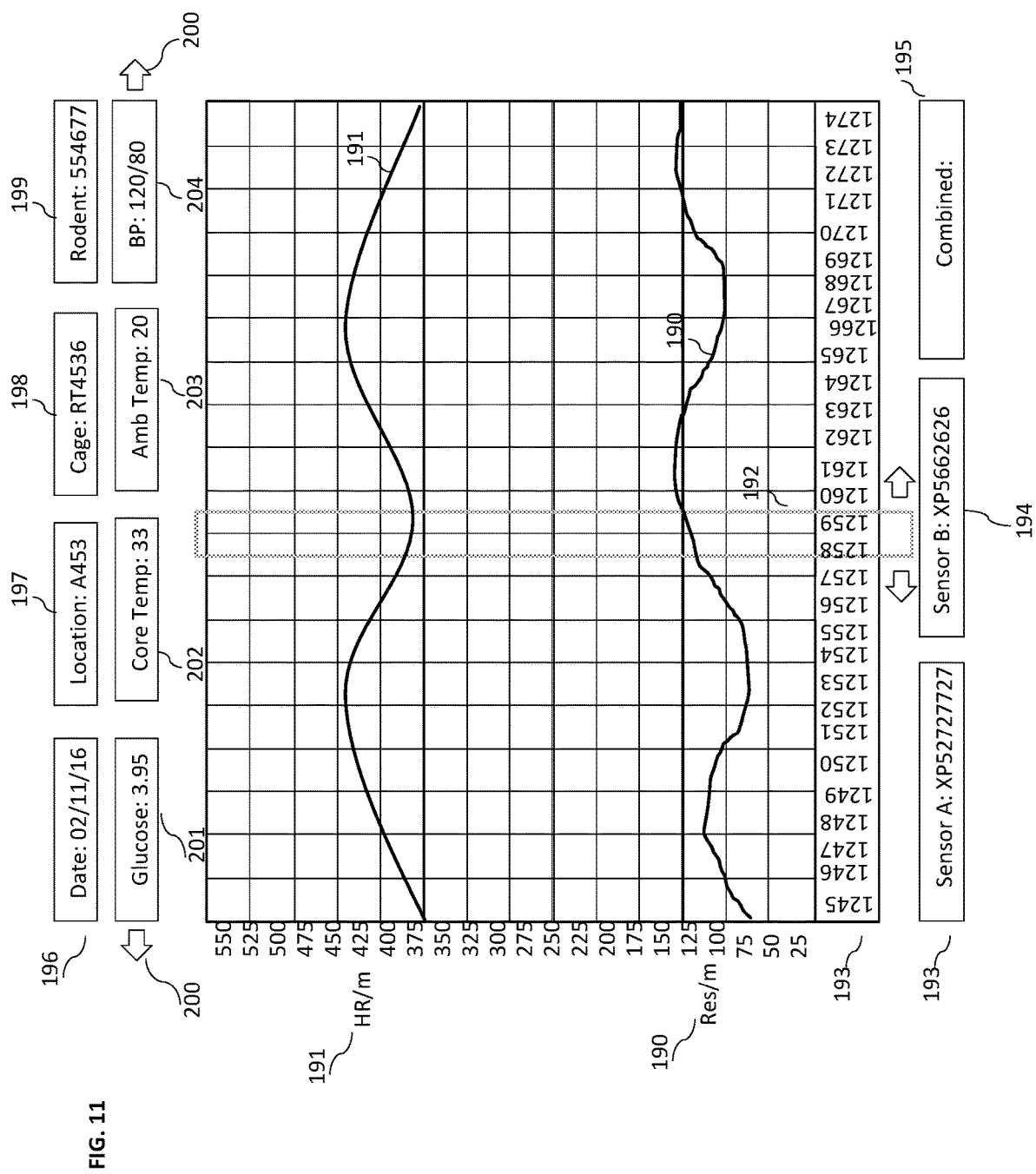
FIG. 11 shows an illustrative reporting system in accordance with one or more aspects of the disclosure.

FIG. 11 shows a reporting system that provides both trending and a snapshot of the results obtained, augmented and processed. In the graph the bottom scale is for respiration rate per minute 190 and the top part of scale is representing heart rate per minute 191. Along the bottom of the graph is a time slide bar 192 based on timed readings of 60 times an hour that allows for the researcher to move the slide bar to specific time intervals of the day 193 or to the beginning of an alarm interval etc. Below the graph, the researcher may select either sensor array A 193 or sensor array B 194 in the cage or a combination of the two 195. Along the top of the graph is the identification row of information related to the specific cage being reviewed including the date 196, cage location 197, cage number 198, and rodent ID 199. Situated directly below is an information scroll bar of all of the possible physiological signs available such as glucose 200, core temperature 202, ambient temperature 203, blood pressure 204, etc. The researcher may scroll 200 through all of the available data that is related to that specific animal and time interval selected 192.

A number of embodiments have been described where it is understood that various modifications may be made without departing from the spirit and scope of the disclosure.

We claim:

1. A system comprising:
    an enclosure;
    at least two sensors, one of which is a UWB radar, located relative to the enclosure;
    a processor configured to receive signals from the two sensors;
    a memory configured to store information contained in the signals received by the processor; and
    a feeding/watering station inside the enclosure, wherein the feeding/watering station comprises:
       a water tube;
       a bracket configured to be attached to the enclosure;
       a paddle;
       a pin attaching the paddle to the bracket;
       a spring positioned to urge the paddle to pivot about the pin,
    wherein the paddle is located below the water tube,
    wherein the paddle further comprises a paddle switch activated by force applied to the paddle causing the paddle to pivot, about the pin, against the urging of the spring,
    wherein UWB radar is located in the paddle and is activated based on activation of the paddle switch, and
    wherein the processor is further configured to monitor, using signals from the UWB radar, a heart rate while an animal is activating the paddle switch.

2. The system according to claim 1, wherein the enclosure is sized to accommodate two or more rodents.

3. The system according to claim 1,
    wherein the processor is configured to determine a quality of the information from at least one of the sensors.

4. The system according to claim 3,
    wherein the processor is configured to, when the information is determined to be a sufficient quality, store the information.

5. The system according to claim 3,
    wherein the processor is further configured to, when the information is determined to be less than sufficient quality, store the information with information regarding the quality of the information.

6. The system according to claim 1, wherein the processor is further configured to determine, from the signals from the UWB radar, heart rate variability.

7. The system according to claim 1, wherein another of the at least two sensors is an ambient temperature sensor.

8. The system according to claim 1, wherein another of the at least two sensors is an RFID sensor.

9. The system according to claim 1, wherein another of the at least two sensors is an accelerometer.

10. The system according to claim 1, wherein another of the at least two sensors is a urine analysis sensor.

11. The system according to claim 1, wherein the processor is further configured to determine, from the signals from the UWB radar, blood pressure.

12. The system according to claim 1, wherein the processor is further configured to:
    based on the information having reached a high confidence factor, store the information.

13. The system according to claim 1, wherein the processor is further configured to:
    store the information and a confidence factor associated with the information.

14. The system according to claim 1, wherein the processor is further configured to:
    determine, using the signals from the UWB radar, whether an animal in the enclosure is deceased.

15. The system according to claim 1, wherein the processor is further configured to:
    determine, using the signals from the sensor other than the UWB radar, one or more environmental conditions.

* * * * *